US00PP23693P2

(12) United States Plant Patent
Bradford

(10) Patent No.: US PP23,693 P2
(45) Date of Patent: Jul. 2, 2013

(54) INTERSPECIFIC TREE NAMED 'GREENSWEET XXI'

(50) Latin Name: ***Prunus* sp.**
Varietal Denomination: Greensweet XXI

(76) Inventor: Lowell Glen Bradford, Le Grand, CA (US)

( * ) Notice: Subject to any disclaimer, the term of this patent is extended or adjusted under 35 U.S.C. 154(b) by 55 days.

(21) Appl. No.: 13/374,015

(22) Filed: Dec. 8, 2011

(51) Int. Cl.
*A01H 5/00* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP14,220 P2 10/2003 Bradford
PP16,461 P2 4/2006 Bradford

*Primary Examiner* — Annette Para

(57) ABSTRACT

The present invention relates to an interspecific tree and more particularly to a new and distinct variety broadly characterized by a medium size, moderately vigorous, hardy, and productive tree. Being self-unfruitful, the present variety requires cross pollination from an apricot, interspecific, or plum that blooms during the mid to late season. The present variety produces a heavy bloom with a moderate amount of pollen to entice good bee activity to facilitate pollination. The fruit matures under the ecological conditions described during the first part of November, with first picking on Nov. 2, 2011. The fruit is uniformly small to medium in size, a green and red two-tone in skin color, clingstone in type, globose with a small apex hump in shape, yellow in flesh color, firm and crisp in texture, and outstandingly sweet in flavor.

1 Drawing Sheet

Botanical classification: *Prunus* sp.
Varietal denomination: 'GREENSWEET XXI'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree which has been denominated varietally as 'GREENSWEET XXI'.

During a typical blooming season I isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2005 one such house containing a 'September Yummy®' plum tree (U.S. Plant Pat. No. 14,220) was crossed by me in this manner. To pollinate this plum tree, I selected bouquets from several sources of apricot and interspecific hybrid trees without keeping specific written details. Upon reaching maturity the fruit from this plum tree was harvested and the seeds were removed, cracked, stratified and germinated as a group with the label "H12". They were grown as seedlings on their own root in my greenhouse and upon reaching dormancy transplanted to a cultivated area of my experimental orchard located near Le Grand, Calif. in Merced County (San Joaquin Valley). During the summer of 2008 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'September Yummy' (U.S. Plant Pat. No. 14,220) plum, by being self-unfruitful and by producing fruit that is firm, juicy, and mostly yellow in flesh color, but is distinguished therefrom by producing fruit that is a red and green two-tone in skin color instead of full red, that is much sweeter in flavor, that is smaller in size, and that matures about fifty days later.

The present variety is most similar to 'Plumsweet IV' (U.S. Plant Pat. No. 16,461) interspecific, by being self-unfruitful and by producing fruit that is very sweet in flavor, juicy, clingstone in type, and two-tone in skin color, but is distinguished therefrom by producing fruit that is purely yellow in flesh color, that is globose with a small apex hump instead of oblong in shape, that is smaller in size, and that matures at least fifty days later.

SUMMARY OF VARIETY

The present interspecific variety is characterized by a medium size, moderately vigorous, hardy, and productive tree. Being self-unfruitful, the present variety requires cross pollination from an apricot, interspecific, or plum that blooms during the mid to late season. The present variety produces a heavy bloom with a moderate amount of pollen to entice good bee activity to facilitate pollination. The fruit matures under the ecological conditions described during the first part of November, with first picking on Nov. 2, 2011. The fruit is uniformly small to medium in size, a green and red two-tone in skin color, clingstone in type, globose with a small apex hump in shape, yellow in flesh color, firm and crisp in texture, and outstandingly sweet in flavor.

DRAWING

The accompanying photograph consists of four whole fruits positioned to display the characteristics of the skin color and form, two half fruits divided to reveal the flesh and stone, one cleaned stone, typical leaves, and one inset depicting the blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of picking ripe on Nov. 2, 2011, on the original tree during its sixth growing season. The flower and bud descriptions were developed during the previous blooming season. All major color code designations are by reference to the Inter-Society Color Council, National Bureau of Standards. Common color names are also used occasionally.

PARENTAGE

Seed parent: 'September Yummy®' (U.S. Plant Pat. No. 14,220).
Pollen parent: Unknown.

TREE

Size: Medium, reaching and maintaining a height of 10' [3.05 m.] and a spread of 4' [1.22 m.] after six growing seasons utilizing typical dormant pruning.
Vigor: Medium vigor, responding typically to irrigation and fertilization. The variety grows about 4' [1.22 m.] of surplus top-growth during the spring and summer. The plant should be grown on a standard commercial rootstock for production purposes.
Growth: Upright and dense.
Form: Pruned to a Parallel "V".
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive, thinning usually necessary.
Fertility: Self-unfruitful, requiring cross pollination by a suitable mid to late seasonal blooming apricot, interspecific, or plum such as 'Black Majesty' plum (U.S. Plant Pat. No. 19,527).
Bearing: No crop failures observed thus far, weather dependent.
Trunk:
- *Size*.—Slender, reaching a maximum diameter of 2¾" [69.9 mm.] after the sixth growing season.
- *Texture*.—Shaggy.
- *Bark color*.—Dark grayish brown [62. d.gy.Br] with Light yellowish brown [76. l.yBr] crevices present.
- *Lenticels*.—Approximate Number Per Square Inch: 12. Color: Brownish orange [54. brO]. Size: ⅛" [3.2 mm.] to ¼" [6.4 mm.]. Shape: Eye-shaped, elongated.

Branches:
- *Size*.—Diameter of main scaffold is 1¼" [31.8 mm.] measured 12" above the first crotch, diameter of limb is ⅞" [22.2 mm.] measured 12" above first fork.
- *Texture*.—Smooth on first and second year wood, increasing roughness with age.
- *Color*.—1st Year Wood Topside: Grayish red [19. gy.R]. 1st Year Wood Underside: Brilliant yellow green [116. brill.YG]. Older Wood: Dark grayish brown [62. d.gy.Br] with Light yellowish brown [76. l.yBr] crevices present.
- *Lenticels*.—Number Per Square Inch: About 40 on second year wood. Color: Light orange yellow [70. l.OY]. Size: 1/64" [0.4 mm.] to 1/16" [1.6 mm.]. Shape: Eye-shaped, elongated.

Leaves:
- *Size*.—Small. Average Length: 3½" [88.9 mm.]. Average Width: 1 9/16" [39.7 mm.].
- *Arrangement*.—Alternate.
- *Thickness*.—Medium.
- *Form*.—Elliptical.
- *Apex*.—Acuminate.
- *Base*.—Acute with an average angle base angle of 60 degrees.
- *Surface*.—Smooth.
- *Color*.—Dorsal Surface: Moderate olive green [125. m.OlG]. Ventral Surface: Moderate yellow green [120. m.YG].
- *Margin*.—Finely serrate.
- *Venation*.—Pinnately net veined.
- *Petiole*.—Average Length: 7/16" [11.1 mm.]. Average Thickness: 1/16" [1.6 mm.]. Color: Light yellow green [119. l.YG] on the bottom side and Grayish red [19. gy.R] on the top side.
- *Stipules*.—Number: Usually 2 per leaf, up to 6 per growing tip. Average Length: ⅜" [9.5 mm.]. Color: Moderate yellow green [120. m.YG] becoming Dark yellowish brown [78. d.yBr] with age.
- *Glands*.—Number: 1 to 4 per leaf, mostly 2. Position: Mostly alternate, positioned at the intersection of the petiole and the leaf blade. Size: Small. Form: Globose. Color: Light yellow green [119. l.YG] becoming Grayish brown [61. gy.Br] in the center with age. Leaf buds — Pointed, medium.

Flower buds:
- *Hardiness*.—Hardy, with respect to central California winters.
- *Diameter*.—Typically 3/16" [4.8 mm.] 1 week before bloom.
- *Length*.—Typically ⅜" [9.5 mm.] 1 week before bloom.
- *Form*.—Not appressed.
- *Surface*.—Pubescent.
- *Tip color*.—White [263. White].

Flowers: Perfect, complete, perigynous, usually a single pistil, typically thirty or more stamens, five sepals and petal locations alternately positioned.
- *Average flower diameter*.—1" [25.4 mm.].
- *Number of petals*.—Five, no double blossoms observed.
- *Petal shape*.—Oval to circular.
- *Petal margin*.—Entire, somewhat wavy.
- *Average petal diameter*.—½" [12.7 mm.].
- *Average petal length*.—9/16" [14.3 mm.].
- *Petal apex*.—Rounded.
- *Petal base*.—Obtuse.
- *Petal color*.—White [263. White] on both sides.

*Anther color*.—Very yellow [82. v.Y].
*Stigma color*.—Light greenish yellow [101. l.gY].
*Sepal color*.—Light yellow green [119. l.YG].
*Sepal length*.—3/16" [4.8 mm.].
*Sepal width*.—5/32" [4.0 mm.].
*Sepal apex*.—Rounded to elliptical to match the width and length.
*Sepal margin*.—Fairly smooth with slight serrations toward the apex.
*Average pistil length*.—9/16" [14.3 mm.].
*Average stamen length*.—7/16" [11.1 mm.].
*Fragrance*.—Moderate.
*Bloom density*.—Heavy.
*Number per cluster*.—2 to 9, average 5.
*Pollen production*.—Moderate, strong enticement to bees.
*Blooming period*.—Medium to late, near 'Santa Rosa' plum (unpatented).
*Onset of bloom*.—One percent on Mar. 3, 2011.
*Date of full bloom*.—Mar. 11, 2011.
*Duration of bloom*.—One to two weeks, dependent on ambient temperature.

FRUIT

Maturity when described: Picking ripe, Nov. 2, 2011.
Date of first picking: Nov. 2, 2011.
Date of last picking: Nov. 16, 2011.
Size: Uniform, small to medium.
*Average diameter axially*.—2⅜" [60.3 mm.].
*Average diameter across cheek plane*.—2¼" [57.2 mm.].
*Average diameter across suture plane*.—2¼" [57.2 mm.].
*Typical weight*.—4.0 ounces [133 grams].
Form: Uniform, globose with a small apex hump, symmetrical.
*Longitudinal section form*.—Circular to slightly oval.
*Transverse section through axial diameter*.—Circular.
Suture: A very shallow trough extending from the base to the apex.
Ventral surface: Rounded, lipped toward the base.
Lips: Equal.
Cavity: Flaring elongated in the suture plane, suture showing on one side, stem indentations occur occasionally.
*Depth*.—⅜" [9.5 mm.].
*Breadth*.—⅞" [22.2 mm.].
Base: Truncate, slightly cordate if viewed parallel to the suture.
Apex: Rounded, with a small hump on most.
Pistil point: An inconspicuous Deep brown [56. deep Br] dot located on a small hump.
Stem: Medium.
*Average length*.—7/16" [11.1 mm.].
*Average width*.—3/32" [2.4 mm.].
Skin:
*Thickness*.—Medium.
*Surface*.—Smooth.
*Tenacity*.—Tenacious to the flesh.
*Astringency*.—Slight.
*Tendency to crack*.—None observed.
*Color*.—A Deep red [13. deep R] and Deep greenish yellow [100. deep gY] two-tone with a moderate amount of Moderate greenish yellow [102. m.gY] freckling throughout.
*Bloom*.—Abundant.
Flesh:
*Color*.—Moderate greenish yellow [102. m.gY] toward the skin and Brilliant greenish yellow [98. brill.gY] toward the stone.
*Surface of pit cavity*.—Covered with Grayish greenish yellow [105. gy.gY] broken fibers when twisted away from stone.
*Amygdalin*.—Moderate.
*Juice*.—Abundant, rich.
*Texture*.—Firm, tough, meaty.
*Fibers*.—Abundant, fine, tender.
*Ripens*.—Fairly even, slightly earlier toward the apex.
*Flavor*.—Very sweet with moderate acid, typically 25 brix.
*Aroma*.—Very slight.
*Eating quality*.—Outstanding.

STONE

Type: Clingstone.
Form: Oval.
Hilum: Narrow to oblong.
Base: Rounded with a notch.
Apex: Acute, with a sharp 1/16" [1.6 mm.] tip.
Sides: Equal.
Surface: Rough throughout with a vertical ridge on each side of the dorsal fin.
External color of stone: Moderate yellowish brown [77. m.yBr] when dry.
Pit wall color when cracked: Strong yellowish brown [74. s.yBr].
Cavity surface color: Light grayish yellowish brown [79. l.gy.yBr].
Average pit wall thickness: 3/32" [2.4 mm.]
Average width: ¾" [19.1 mm.].
Average length: 1" [25.4 mm.].
Average breadth: 7/16" [11.1 mm.].
Tendency to split: None observed.
Kernel:
*Form*.—Oval.
*Skin color*.—Strong yellowish brown [74. s.yBr].
*Pellicle color*.—Moderate yellowish brown [77. m.yBr].
*Vein color*.—Deep yellowish brown [75. deep yBr].
*Taste*.—Bitter.
*Viable*.—Yes.
*Average width*.—⅜" [9.5 mm.].
*Average length*.—⅝" [15.9 mm.].
*Amygdalin*.—Moderate.

USE

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'Plumsweet IV' (U.S. Plant Pat. No. 16,461) interspecific, by being self-unfruitful and by producing fruit that is very sweet in flavor, juicy, clingstone in type, and two-tone in skin color, but is distinguished therefrom by producing fruit that is purely yellow in flesh color, that is globose with a small apex hump instead of oblong in shape, that is smaller in size, and that matures at least fifty days later.

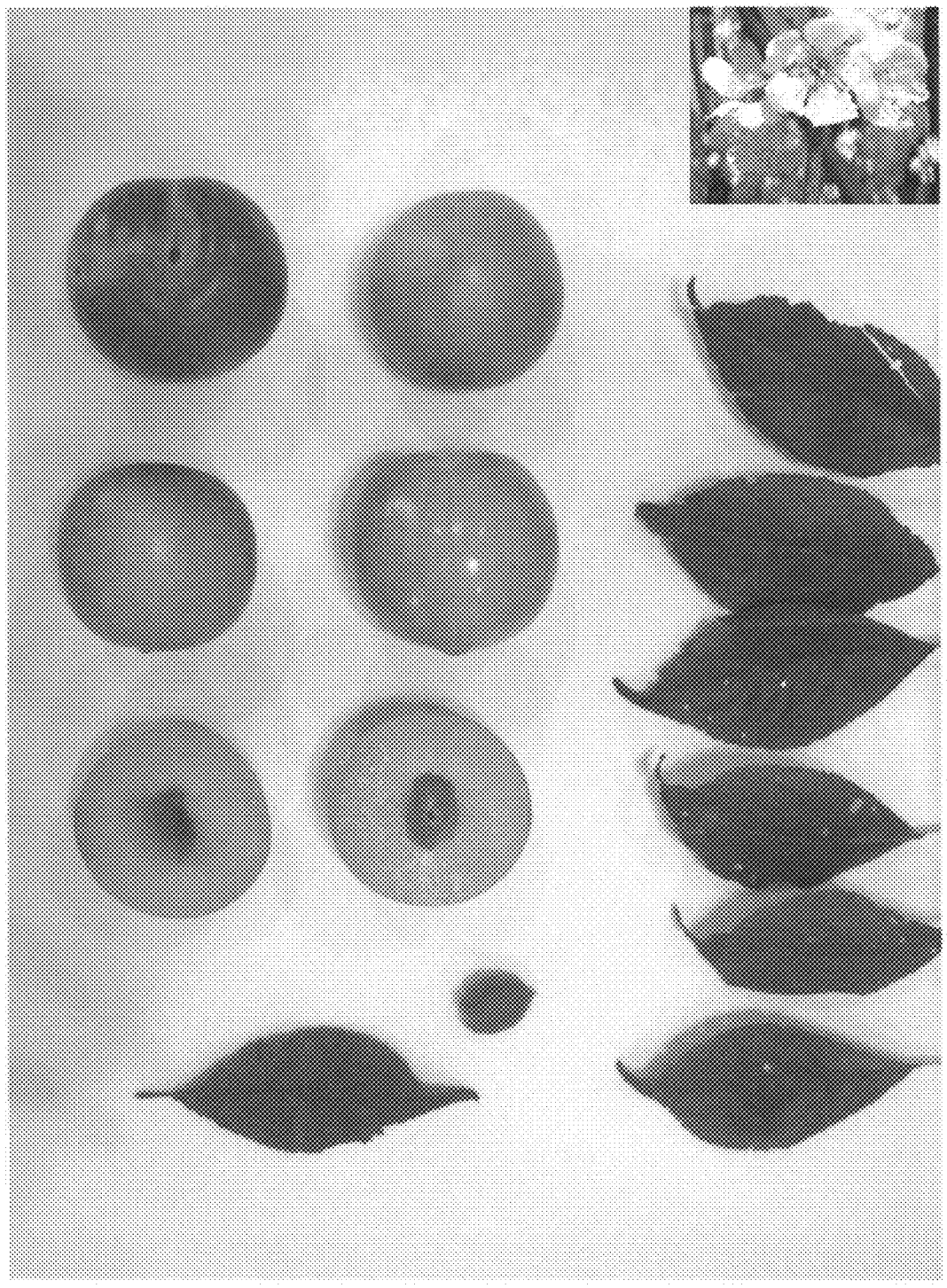

* * * * *